US010966960B2

(12) United States Patent
Moolenaar

(10) Patent No.: US 10,966,960 B2
(45) Date of Patent: *Apr. 6, 2021

(54) MEDICAL TREATMENT COMPRISING ENTERAL ADMINISTRATION OF EDARAVONE

(71) Applicant: Treeway TW001 B.V., Rotterdam (NL)

(72) Inventor: Sytske Hyke Moolenaar, Rotterdam (NL)

(73) Assignee: TREEWAY TW001 B.V., Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,497

(22) Filed: Jul. 12, 2019

(65) Prior Publication Data

US 2019/0328711 A1 Oct. 31, 2019

Related U.S. Application Data

(63) Continuation of application No. PCT/EP2017/067005, filed on Jul. 6, 2017.

(30) Foreign Application Priority Data

Jan. 17, 2017 (EP) ..................................... 17151741

(51) Int. Cl.
| A61K 31/4152 | (2006.01) |
|---|---|
| A61K 9/16 | (2006.01) |
| A61K 9/20 | (2006.01) |
| A61K 9/10 | (2006.01) |

(52) U.S. Cl.
CPC ............ *A61K 31/4152* (2013.01); *A61K 9/10* (2013.01); *A61K 9/1611* (2013.01); *A61K 9/1623* (2013.01); *A61K 9/1641* (2013.01); *A61K 9/2009* (2013.01); *A61K 9/2018* (2013.01); *A61K 9/2031* (2013.01)

(58) Field of Classification Search
None
See application file for complete search history.

(56) References Cited

FOREIGN PATENT DOCUMENTS

| CN | 1449754 | * | 10/2003 |
|---|---|---|---|
| CN | 1449754 A | | 10/2003 |
| CN | 100352520 C | | 12/2007 |
| CN | 100358520 C | | 1/2008 |
| CN | 101953832 A | | 1/2011 |
| CN | 102349893 | * | 2/2012 |
| CN | 102349893 A | | 2/2012 |
| CN | 103251554 | | 8/2013 |
| CN | 105816423 | * | 8/2016 |
| EP | 1 405 637 A | | 4/2004 |
| EP | 1 714 960 A | | 10/2006 |
| EP | 2 754 440 A | | 7/2014 |
| WO | WO-2012/019381 | | 2/2012 |
| WO | WO-2018/133957 A1 | | 7/2018 |
| WO | WO-2018/134243 | | 7/2018 |
| WO | WO-2019/008144 A1 | | 1/2019 |

OTHER PUBLICATIONS

Awad et al., "The history of 0.9% Saline", Clinical Nutrition, 2008, vol. 27, pp. 197-188 (10 pages).
Cruz, Martin Paspe, "Edaravone (Radicava): A Novel Neuroprotective Agent for the Treatment of Amyotrophic Lateral Sclerosis", Drug Forecast, vol. 43, N. 1, Jan. 2018 (4 pages).
Hayashi et al., "Efficacy of Edaravone, a Free Radical Scavenger, on Left Ventricular Function and Structure in Diabetes Mellitus", Journal of Cardiovascular Pharmacology, vol. 41, No. 6, Jun. 2003 (7 pages).
International Preliminary Report on Patentability for PCT/EP2017/067005 dated May 9, 2019 (9 pages).
International Preliminary Report on Patentability for PCT/EP2018/051097 dated May 14, 2019 (14 pages).
International Preliminary Report on Patentability for PCT/EP2018/068396 dated Oct. 23, 2019 (15 pages).
International Search Report and Written Opinion of the International Searching Authority for PCT/EP2017/067005 dated Oct. 4, 2017 (11 pages).
International Search Report and Written Opinion of the International Searching Authority for PCT/EP2018/051097 dated Apr. 26, 2018 (12 pages).
International Search Report and Written Opinion of the International Searching Authority for PCT/EP2018/068396 dated Oct. 8, 2018 (11 pages).
Ishizawa et al., "An antioxidant treatment potentially protects myocardial energy metabolism by regulating uncoupling protein 2 expression in a chronic β-adrenergic stimulation rat model", Life Sciences, vol. 78, 2006 (9 pages).

(Continued)

*Primary Examiner* — Danah Al-Awadi
(74) *Attorney, Agent, or Firm* — Foley & Lardner LLP

(57) ABSTRACT

A solid water-dispersible pharmaceutical composition for use in the treatment of a disease is disclosed. The treatment comprises dispersing the pharmaceutical composition into an aqueous liquid to produce an enterally administrable liquid containing at least 0.5 grams of the pharmaceutical composition and at least 0.3 g/l of edaravone, followed by enterally administering the enterally administrable liquid to a human patient in an amount providing a dose of 30-300 mg edaravone. The pharmaceutical composition comprises 2-50 wt. % of 3-methyl-1-phenyl-2-pyrazolin-5-one (edaravone) and 3-50 wt. % of a water soluble alkalizing agent. This solid edaravone containing composition can easily be dispersed in aqueous liquid to prepare an aqueous edaravone solution that can be ingested by a patient. The solid composition of the present invention offers the advantage that edaravone dissolves very rapidly when the composition is introduced into water and that the enterally administrable liquid so obtained has high oral bioavailability.

20 Claims, No Drawings

(56) References Cited

OTHER PUBLICATIONS

Jiao et al., "Edaravone alleviates Alzheimer's disease-type pathologies and cognitive deficits", Proceedings National Academy of Sciences PNAS, vol. 112, No. 16, Apr. 6, 2015 (6 pages).
Jiao et al., "Supporting Information" for Edaravone alleviates Alzheimer's disease-type pathologies and cognitive deficits, Proceedings National Academy of Sciences PNAS, Apr. 6, 2015 (10 pages).
Mitsubishi Tanabe Pharma Corporation, "Radicut Injection 30mg", Jun. 1, 2015 (8 pages).
Parikh et al., "Development of a novel oral delivery system of edaravone for enhancing bioavailability", International Journal of Pharmaceutics, vol. 515, No. 1-2, Oct. 24, 2016 (11 pages).
Parikh et al., "Lipid-based nanosystem of edaravone: development, optimization, characterization and in vitro/in vivo evaluation", Drug Delivery, vol. 24, No. 1, 2017 (17 page).
Rong et al., "Hydroxpropyl-sulfobutyl-β-cyclodextrin improves the oral bioavailability of edaravone by modulating drug efflux pump of enterocytes", Journal of Pharmaceutical Sciences, vol. 103, Issue 2, Feb. 2014 (13 pages).
Sato et al., "A Novel Administration Route of Edaravone—II: Mucosal Absorption of Edaravone from Edaravone/Hydroxypropyl-Beta-Cyclodextrin Complex Solution Including L-Cysteine and Sodium Hydrogen Sulfite", Pharmacology: International Journal of Experimental and Clinical Pharmacology, vol. 85, No. 2, Jan. 31, 2010 (7 pages).

* cited by examiner

MEDICAL TREATMENT COMPRISING ENTERAL ADMINISTRATION OF EDARAVONE

CROSS-REFERENCE TO RELATED PATENT APPLICATIONS

This application is a continuation of International Patent Application No. PCT/EP2017/067005, filed Jul. 6, 2017, which claims the benefit of and priority to European Application No. 17151741.0, filed Jan. 17, 2017. The entire disclosure of each application is incorporated by reference herein.

FIELD OF THE INVENTION

This invention relates to a solid pharmaceutical composition containing 3-methyl-1-phenyl-2-pyrazolin-5-one (edaravone) for use in medical treatment, said treatment comprising dispersing the solid pharmaceutical composition into an aqueous liquid to produce an enterally administrable liquid, followed by enteral administration of the enterally administrable liquid to a human patient.

The solid edaravone compositions of the present invention are very stable, and once the composition has been dissolved in aqueous liquid it is easy to ingest and provides edaravone with high oral bioavailability.

Examples of diseases that can be treated by enterally administering the present composition include neurodegenerative diseases, such as amyotrophic lateral sclerosis (ALS) and Alzheimer's disease; cerebral amyloid angiopathy (CAA); auto-immune diseases, such a multiple sclerosis (MS); myocardial infarction and cerebrovascular diseases, such as ischemic stroke.

BACKGROUND OF THE INVENTION

ALS is a neurodegenerative disorder, which affects both the upper motor neurons, located in the brain, and the lower motor neurons, located in the spinal cord and brainstem. Upper motor neuron degeneration generally causes muscle spasticity, while lower motor neuron degeneration causes muscle weakness, muscle atrophy and twitching.

Early symptoms of ALS typically include muscle weakness in the hands, arms, legs or feet, causing weakness or spasticity in these body parts. The disease may also present itself in the muscles controlling speech or swallowing resulting in difficult chewing, speaking, swallowing, and breathing. As the disease progresses, it spreads to other parts of the body leading to progressive muscle weakness and paralysis. ALS patients ultimately lose their ability to initiate and control all voluntary movement and neuromuscular respiratory failure makes breathing increasingly difficult. Early symptoms and the development of the disease vary with each individual.

Sensory nerves and the autonomic nervous system remain unaffected, leaving hearing, sight, touch, smell, and taste intact as well as the involuntary muscles such as those that control heartbeat, gastrointestinal tract, bowel and bladder function. Cognitive function generally remains unaffected as well.

Most people who develop ALS are between the ages of 40 and 70, but the disease can also occur at a younger age. Prevalence has been found to increase with age. Although ALS is classified as a rare disease it is the most common motor neuron disease. About one or two out of 100,000 people develop ALS each year while the prevalence of ALS is estimated to be about two cases per 100,000 population, with increasing numbers due to the aging population.

Riluzole is currently the only approved drug for ALS. Its effect is believed to reside in its potential to reduce signaling of glutamate, a neurotransmitter that has been found to be present in higher levels in people with ALS. The drug has been found to have a limited beneficial effect on the symptoms of ALS as well on the progression of the disease. It would improve survival, but only to a modest extent.

Other medications prescribed to ALS patients are aimed at improving quality of life and relieving symptoms of ALS such as muscle cramps and spasms, constipation, fatigue, excessive salivation and phlegm, pain, depression, and sleep problems.

Edaravone is a nootropic and neuroprotective agent used to aid neurological recovery following acute brain ischemia and subsequent cerebral infarction. It acts as a potent antioxidant and strongly scavenges free radicals, protecting against oxidative stress and neuronal apoptosis.

EP-A 1 405 637 describes the use of edaravone in the treatment of motor neuron diseases, including ALS.

EP-A 1 714 960 concerns the use of edaravone in the treatment of ALS with one or more drug holiday periods during the period of treatment.

EP-A 2 754 440 describes the use of edaravone for treating ALS in specific patient populations, wherein the agent is administered by repeating a 14-day administration period and a 14-day drug holiday period, or by establishing an initial 14-day administration period and an initial 14-day drug holiday period and then repeating an administration period for 10 out of 14 days and a 14-day drug holiday period.

CN 1449754 describes the preparation of a pharmaceutical composition by mixing edaravone with a pharmacologically acceptable alkaline substance and water to prepare a clear solution, followed by freeze-drying to produce a freeze-dried powder that can be used to prepare a liquid formulation for injection.

CN 103251554 relates to a stable edaravone injection and a preparation method thereof. The edaravone injection comprises an osmotic pressure adjustor comprising sodium chloride, phosphoric acid, phosphoric acid, citric acid monohydrate and sodium hydrogen sulfite, a pH adjustor, a dissolving adjuvant and an anti-oxygen, wherein sodium hydroxide is not only used as the pH adjustor, but also has the effect of the dissolving adjuvant, so that the dissolving time of main medicines is greatly shortened.

It is well recognized in the prior art that the oral bioavailability of edaravone is low and investigations have been carried out in order to provide oral formulations of edaravone that achieve improved oral bioavailability.

Rong et al. (*Hydroxypropyl-Sulfobutyl-β-Cyclodextrin Improves the Oral Bioavailability of Edaravone by Modulating Drug Efflux Pump of Enterocytes,* Journal of Pharmaceutical Sciences (2013), DOI 10.1002/jps.23807, 1-13) describe a study in which the effect of hydroxypropyl-sulfobutyl-β-cyclodextrin on the bioavailability and intestinal absorption of edaravone was investigated. It was found that the inclusion complex of edaravone-cyclodextrin improved the water solubility of edaravone and enhanced the bioavailability of bioavailability of edaravone in rats. Table 2 of this article shows that the absolute bioavailability ($F_{abs}$) of orally administered 'raw' edaravone (suspended with 0.5% CMC-Na) was only 5.23% (compared to 100% bioavailability of intravenously administered edaravone). Table 2 further shows that the oral bioavailabity of edaravone could be improved by more than factor 10 by complexing edaravone with cyclodextrin.

Parikh et al. (*Development of a novel oral delivery system of edaravone for enhancing bioavailability*, International Journal of Pharmaceutics 515 (2016) 490-500) discuss the development of an oral delivery system of edaravone. The authors describe a Novel Oral Delivery System of edaravone (NODS) that is made up of a mixture of Labrasol and an acidic aqueous system that was optimized on the basis of a solubility and stability study. The NODS delivery system contained 30 mg/mL of edaravone. The in-vivo oral bioavailability of the NODS delivery system was investigated in adult rats using an equivalent dose of 30 mg/kg edaravone. It was found that the oral bioavailability of the NODS delivery system was 5.7 times higher than that of an edaravone suspension containing 30 mg/mL edaravone and 0.5% sodium carboxymethyl cellulose (see Table 2).

Parikh et al. (*Lipid-based nanosystem of edaravone: development, optimization, characterization and in vitro/in vivo evaluation*, Drug Delivery 24(1); (2017), 962-978) describe a study that aimed at enabling oral use of edaravone by developing a lipid-based nanosystem (LNS). The components of LNS including oil, surfactants, and co-surfactants were selected based on their potential to maximize the solubilization in gastrointestinal (GI) fluids, reduce its glucuronidation and improve transmembrane permeability. A liquid LNS (L-LNS) in the form of a micro-emulsion was prepared, comprising Capryol™ PGMC (Oil), Cremophor® RH 40:Labrasol®:TPGS 1000 (1:0.8:0.2) (Surfactant) and Transcutol® P (Co-surfactant). It was found that the oral bioavailability of the L-LNS was almost 11 times higher than that of an edaravone suspension containing 30 mg/mL edaravone and 0.5% sodium carboxymethyl cellulose (see Table 3).

WO 2012/019381 describes an oral pharmaceutical composition containing edaravone and cyclodextrin in a weight ratio of edaravone to cyclodextrin of 1:6-100. The preparation method comprises the following steps:

mixing β-cyclodextrin or the mixture of cyclodextrins containing β-cyclodextrin with 1-5 times of water in weight,
  adding edaravone or its solution in organic solvent into the cyclodextrin solution,
  grinding or stirring, and
  evaporating water at the temperature no higher than 60° C., drying by decompression.

CN 101 953 832 describes an oral pharmaceutical composition comprising cyclodextrin in combination with edaravone. The examples of the Chinese patent application describe tablets, capsules and granules containing cyclodextrin-edaravone complex.

CN 105 816 423 describes various drug delivery systems comprising edaravone. The examples of this Chinese patent application describe oral administration of edaravone (30 mg.kg) to rats using a self-micro-emulsifying drug delivery systems (SMEDDS).

Edaravone is currently administered intravenously, using ampoules, the content of which is diluted with physiological fluid. Intravenous injection however is a less attractive route of administration as it requires the presence of a medical practitioner and therefore does not allow self-administration. Furthermore, many patients do not like to receive a drug by injection.

Edaravone is instable in aqueous solution as it is prone to decomposition by oxidation, showing decreased stability with increased concentration. Aqueous solutions of edaravone, such as injection formulations, are challenging to prepare because Edaravone is only sparingly soluble in water (appr. 1.85 mg/mL at 25° C.) and because it dissolves very slowly.

SUMMARY OF THE INVENTION

Amongst the various ways of drug delivery, oral delivery is still the most attractive and acceptable route of administration for active pharmaceutical ingredients. The oral route is preferred because of its convenience resulting in high levels of patient acceptance and long term compliance, which in turn increases the therapeutic value of the drug. In most instances, it allows the patient to self-administer the drug without the help of a medical practitioner.

It is therefore desirable to provide edaravone dosage forms that can be administered by the oral route. Traditional oral dosage forms such as tablets and capsules, however, pose problems to patients who have difficulty in swallowing. This is often the case with e.g. ALS patients.

The inventors have designed a solid edaravone containing composition that can easily be dispersed in aqueous liquid to prepare an aqueous edaravone solution that can be ingested by a patient shortly after preparation. The solid composition of the present invention offers the advantage that edaravone dissolves very rapidly when the composition is introduced into water.

The inventors have unexpectedly discovered that the rate at which edaravone dissolves in water is increased substantially in the presence of an alkalizing agent. Although the inventors do not wish to be bound by theory, it is believed that when edaravone is added to water in concentrations of 0.3 g/l or more, this results in a significant pH reduction as edaravone acts as a weak acid. Because edaravone dissolves more slowly at lower pH, the dissolution rate of edaravone rapidly decreases when the dose in which edaravone is introduced in water is increased. The inventors have found that solid formulations containing edaravone in combination with an alkalizing agent achieve high edaravone dissolution rates, especially when dosed into water at concentrations equivalent to at least 0.3 grams edaravone per liter.

The inventors have further discovered that aqueous edaravone solutions prepared with the solid pharmaceutical formulation of the present invention have a surprisingly high oral bioavailability. Whereas the aforementioned article by Rong et al. reported an absolute bioavailability of orally administered 'raw' edaravone of only 5.23%, the inventors have observed an absolute bioavailability of about 35% for the aqueous edaravone solutions prepared with the present solid pharmaceutical composition.

Thus, one aspect of the invention relates to a solid water-dispersible pharmaceutical composition for use in the treatment of a disease, said treatment comprising dispersing the pharmaceutical composition into an aqueous liquid to produce an enterally administrable liquid containing at least 0.5 grams of the pharmaceutical composition and at least 0.3 g/l of edaravone, followed by enterally administering the enterally administrable liquid to a human patient in an amount providing a dose of 30-300 mg edaravone, said pharmaceutical composition comprising:

2-50 wt. % of 3-methyl-1-phenyl-2-pyrazolin-5-one (edaravone); and
  3-50 wt. % of water soluble alkalizing agent;

wherein the edaravone in this pharmaceutical composition fully dissolves when the composition is added to demineralized water of 25° C. in a concentration equivalent to an edaravone concentration of 1.4 g/l, and wherein the pH of this solution at 25° C. is at least 0.5 pH units higher than the pH of a solution having the same edaravone concentration and consisting exclusively of edaravone and demineralized water.

The solid edaravone composition of the present invention offers the additional advantage it is very stable, especially if the composition is packaged in a sealed sachet or container. Examples of modes of enteral administration that may be employed include oral and gastric administration. Gastric introduction involves the use of a tube through the nasal passage (NG tube) or a tube in the abdomen leading directly to the stomach (PEG tube).

DETAILED DESCRIPTION OF THE INVENTION

A first aspect of the present invention relates to a solid water-dispersible pharmaceutical composition for use in the treatment of a disease, said treatment comprising dispersing the pharmaceutical composition into an aqueous liquid to produce an enterally administrable liquid containing at least 0.5 grams of the pharmaceutical composition and at least 0.3 g/l of edaravone, followed by enterally administering the enterally administrable liquid to a human patient in an amount providing a dose of 30-300 mg edaravone, said pharmaceutical composition comprising:

2-50 wt. % of 3-methyl-1-phenyl-2-pyrazolin-5-one (edaravone); and 3-50 wt. % of water soluble alkalizing agent;

wherein the edaravone in this pharmaceutical composition fully dissolves when the composition is added to demineralized water of 25° C. in a concentration equivalent to an edaravone concentration of 1.4 g/l and wherein the pH of this solution at 25° C. is at least 0.5 pH units higher than the pH of a solution having the same edaravone concentration and consisting exclusively of edaravone and demineralized water.

The term "edaravone" as used herein refers to the substance 3-methyl-1-phenyl-2-pyrazolin-5-one.

The term "water soluble" as used herein, unless indicated otherwise, refers to materials having a solubility in demineralized water of 25° C. of more than 20 g/l.

The term "water insoluble" as used herein, unless indicated otherwise, refers to materials having a solubility in demineralized water of 25° C. of less than 1 g/l.

The term "treatment" as used herein encompasses both therapeutic and palliative treatment.

The term "filler" as used herein refers to pharmaceutically acceptable inert material that provides desired bulk, flow and/or compression characteristics. Examples of suitable fillers include monosaccharides disaccharides and oligosaccharides such as glucose, fructose, saccharose, lactose, raffinose, trehalose and dextrates; and sugar alcohols such as mannitol, sorbitol, maltitol, xylitol and lactitol; and combinations of these components.

The term "disintegrant" as used herein refers to a pharmaceutically acceptable material that has wicking and/or swelling properties when it comes in contact with water. Examples of suitable disintegrants include povidone, crospovidone, starch, pregelatinized starch, sodium starch glycolate, hydroxypropyl starch, microcrystalline cellulose, carboxymethylcellulose sodium or calcium, croscarmellose sodium, polacrilin potassium, low-substituted hydroxypropylcellulose, sodium or calcium alginate, docusate sodium, methylcellulose, agar, guar gum, chitosan, alginic acid, sodium bicarbonate and combinations thereof.

The term "effervescent" as used herein refers to a pharmaceutically acceptable component that is a capable of generating gas when it comes into contact with water. An example of a suitable effervescent are combinations of alkaline carbonate and organic acid, such as sodium bicarbonate and citric acid.

The term "binder" as used herein refers to a pharmaceutically acceptable component that is capable of causing adhesion of powder particles within granules. Examples of suitable (wet) binders include maltodextrin, dextrin, ethylcellulose, methylcellulose, hypromellose, hydroxylpropyl cellulose, sodium carboxymethyl cellulose, polyvinylpyrrolidone and hydrocolloids such as acacia, alginates, carrageenan, dextran, furcellaran, pectin, gelatin, gum agar, locust bean gum, gum ghatti, guar gum, tragacanth, gum Arabic, xanthan gum, karaya gum, tara gum, cellulose derivatives, starch derivatives, polyvinyl alcohol/polyethylene glycol graft copolymers combinations thereof.

According to a particularly preferred embodiment, the pharmaceutical composition when added to demineralized water of 25° C. in a concentration equivalent to an edaravone concentration of 1.4 g/l produces a solution having a pH of at least 6.0, more preferably of at least 6.5, more preferably of at least 6.8. The pH of the solution that is produced in the aforementioned manner typically does not exceed 9.0, more preferably does not exceed 8.8 and most preferably does not exceed 8.5.

The pharmaceutical composition of the present invention preferably is a powder or a tablet. Here the term "powder" also encompasses granulates.

In case the pharmaceutical composition is a powder, edaravone is preferably present in a concentration of 3-25 wt. %, more preferably of 4-20 wt. % and most preferably of 6-18 wt. %.

In case the pharmaceutical composition is a tablet, edaravone is preferably present in a concentration of 4-40 wt. %, more preferably of 8-35 wt. % and most preferably of 10-30 wt. %.

According to a particularly preferred embodiment the composition is a powder. Typically, the powder has a mass weighted average particle size in the range of 30 to 1000 μm, more preferably in the range of 40 to 950 μm, most preferably in the range of 50 to 900 μm. The mass weighted average particle size can suitably be determined using a set of sieves of different mesh sizes.

In a preferred embodiment, the pharmaceutical composition is a powder in the form of granulate. Preferably the granulate has a mass weighted average particle size in the range of 100 to 1000 μm, more preferably of 150 to 950 μm, most preferably of 200 to 900 μm.

The water soluble alkalizing agent preferably present in the pharmaceutical composition in a concentration of 4-45 wt. %, more preferably of 5-40 wt. % and most preferably of 6-35 wt. %.

The pharmaceutical composition preferably contains less than 5 wt. %, more preferably less than 3 wt. % and most preferably less than 1 wt. % water-insoluble material.

Preferably, the pharmaceutical composition additionally contains 25-95 wt. % of excipients selected from filler, disintegrant, effervescent, binder and combinations thereof. More preferably, the pharmaceutical composition contains 40-85 wt. % of these excipients.

According to a particularly preferred embodiment, the pharmaceutical composition contains at least 30 wt. %, more preferably at least 35 wt. % and most preferably at least 40 wt. % water-soluble filler.

According to a particularly preferred embodiment, the pharmaceutical composition contains at least 30 wt. % of one or more polyols, more preferably at least 30 wt. % of one or more polyols selected from mannitol, sorbitol, xylitol, maltitol, lactitol and combinations thereof. Most preferably, the pharmaceutical composition contains at least 30 wt. % of mannitol.

The pharmaceutical compositions of the present invention preferably contains 0.5-15 wt. %, more preferably 0.8-12 wt. %, most preferably 1-10 wt. % of surfactant. More preferably, the composition contains at least 0.5 wt. %, more preferably at least 0.8 wt. % and most preferably at least 1 wt. % of nonionic surfactant.

The nonionic surfactant is preferably selected from Poloxamers, polysorbates and combinations thereof. Poloxamer is a nonionic triblock copolymers composed of a central hydrophobic chain of polyoxypropylene flanked by two hydrophilic chains of polyoxyethylene.

Surfactant is preferably present in the pharmaceutical composition in a concentration of 5-100% by weight of edaravone, more preferably in a concentration of 8-70% by weight of edaravone, most preferably in a concentration of 15-50% by weight of edaravone.

The pharmaceutical composition of the present invention preferably comprises edaravone in the form of micronized particles. Typically, at least 90 volume % of the edaravone is present in the form of micronized particles having a particle size of less than 100 μm, more preferably in the form of micronized particles having a particle size in the range of 0.1 to 60 μm and most preferably in the form of micronized particles having a particle size in the range of 0.2 to 50 μm. The particle size distribution of the micronized edaravone particles can suitably be determined by laser powder diffraction using a MALVERN 3000™ particle size analyzer, using the AERO S dry powder disperser (sample amount: 200-300 mg; analysis model: general purpose; Scattering model: Fraunhofer; Venturi Type: standard; Pressure: 1 bar; Feed rate: 40).

The micronized particles of edaravone may be present in the pharmaceutical composition in the form of discrete particles and/or as part of agglomerates of edaravone micronized particles or of agglomerates of edaravone micronized particles and other particulate pharmaceutically acceptable components.

The water-soluble alkalizing agent in the pharmaceutical composition is preferably selected from oxides and hydroxides of alkaline metals; oxides and hydroxides of alkali-earth metals; $Al(OH)_3$; $Fe_2O_3$; salts of weak organic and weak inorganic acids, alkaline amines; alkaline amino acids; and combinations thereof. The oxides and hydroxides of alkaline metals are preferably selected from NaOH, KOH, LiOH and combinations thereof. The oxides and hydroxides of alkali-earth metals are preferably selected from $Ca(OH)_2$, CaO, $Mg(OH)_2$ MgO and combinations thereof. The salts of weak organic and weak inorganic acids are preferably selected from carbonate, bicarbonate, borate, carboxylate (e.g. lactate, citrate, acetate, formate and oxalate), phosphate, sulfate and combinations thereof. The alkaline amines are preferably selected from tris(hydroxymethyl)aminomethane, ethanolamine, diethanolamine, triethanolamine, N-methyl-glucamine, glucosamine, ethylenediamine, diethylamine, triethylamine, isopropylamine, diisopropylamine, ammonia and combinations thereof. The alkaline amino acids are preferably selected from arginine, histidine, lysine and combinations thereof.

The present invention also encompasses the use of the above mentioned water-soluble alkalizing agents in the form of pharmaceutically acceptable salts and hydrates.

In accordance with one preferred embodiment, the water-soluble alkalizing agent is a base having a $pK_a$ at 20° C. of at least 7, more preferably in the range of 7.5 to 12 and most preferably in the range of 7.7 to 11 In case the water-soluble alkalizing agent is a polyprotic acid that can lose i protons, the agent has at least one $pK_{ai}$ within the aforementioned ranges.

According to a particularly preferred embodiment, the water-soluble alkalizing agent is selected from tris(hydroxymethyl)aminomethane, phosphates (e.g. $Na_3PO_4$) and combinations thereof.

According to a particularly preferred embodiment, the pharmaceutical composition of the present invention comprises edaravone and water soluble alkalizing agent in particulate form. The pharmaceutical composition can be a simple blend of these particulate ingredients. Alternatively, the pharmaceutical composition may comprise granules that contain both these particulate components or it may comprise a combination of two different granules, e.g. granules containing the edaravone and granules containing the water soluble alkalizing agent.

According to one preferred embodiment, the pharmaceutical composition contains a mixture of at least three different powders, including:
  2-50 wt. % of edavarone particles having a edaravone content of at least 50 wt. % and a particle size in the range of 2-120 μm;
  3-50 wt. % of alkalizing particles, said alkalizing particles containing at least 50 wt. % of alkalizing agent and having a particle size in the range of 10-750 μm;
  25-95 wt. % of filler particles containing at least 90 wt. % of water soluble filler and having a particle size in the range of 10-750 μm.

According to a further preferred embodiment, the pharmaceutical composition contains at least 10 wt. %, more preferably at least 30 wt. % and most preferably at least 50 wt. % of granules having a diameter in the range of 80 to 1200 μm, said granules comprising:
  2-50 wt. % of edaravone; and
  3-50 wt. % of water soluble alkalizing agent;
  25-95 wt. % of water soluble filler.

Preferably, the combination of edaravone, water soluble alkalizing agent and water soluble filler constitutes at least 80 wt. %, more preferably at least 85 wt. % and most preferably at least 90 wt. % of the aforementioned granules.

According to an alternative preferred embodiment, the pharmaceutical composition comprises a combination of at least two different granules, including:
  at least 5 wt. % a edaravone granules having a diameter in the range of 80 to 1200 μm, said edaravone granules containing:
    3-70 wt. % of edaravone;
    0-5 wt. %, preferably 0 wt. % of water soluble alkalizing agent and
    30-97 wt. % of water soluble filler;
  at least 5 wt. % of alkalizing granules having a diameter in the range of 80 to 1200 μm, said edaravone granules containing:
    7-80 wt. % of water soluble alkalizing agent;
    0-5 wt. %, preferably 0 wt. % edaravone; and
    20-93 wt. % of water soluble filler.

Preferably, the combination of edaravone, water soluble alkalizing agent and water soluble filler constitutes at least 80 wt. %, more preferably at least 85 wt. % and most preferably at least 90 wt. % of the aforementioned combination of granules.

The present treatment preferably comprises oral or gastric administration of the enterally administrable liquid. Most preferably, the treatment comprises oral administration of said liquid.

According to a particularly preferred embodiment, the pharmaceutical composition according to the invention is used in the treatment of neurodegenerative diseases; cerebral amyloid angiopathy (CAA); auto-immune diseases; myocardial infarction or a cerebrovascular disease. More preferably, the composition is used in the treatment of neurodegenerative diseases or cerebrovascular diseases.

Examples of neurodegenerative diseases that can be treated in accordance with the present invention include amyotrophic lateral sclerosis (ALS) and Alzheimer's disease.

The pharmaceutical composition of the present invention is particularly suited for use in the treatment of ALS.

According to a particularly preferred embodiment, the present treatment of a disease comprises palliative treatment.

The aqueous liquid that is used in the preparation of the enterally administrable edaravone containing liquid typically contains at least 80 wt. % water, more preferably at least 90 wt. % and water. Examples of aqueous liquids that can be employed include mineral water, tap water, cold beverages (including milk) and hot beverages. Most preferably, the aqueous liquid is mineral water or tap water.

In accordance with a particularly preferred embodiment, the aforementioned treatment comprises enterally administering the enterally administrable liquid in a dosage of 10 to 300 ml, more preferably in a dosage of 20 to 250 ml and most preferably in a dosage of 30 to 200 ml.

The treatment according to the present invention typically comprises dispersing 1 part by weight of the pharmaceutical composition into 20 to 200 parts by weight of the aqueous liquid, more preferably 30 to 150 parts by weight of the aqueous liquid and most preferably 40 to 100 parts by weight of the aqueous liquid.

The enterally administrable liquid that is prepared in the present treatment typically contains 0.5-6 g, more preferably 0.8-5 g and most preferably 1-4 g of the pharmaceutical composition.

The enterally administrable liquid used in the present treatment preferably contains at least 500 mg/l, more preferably 800-3,000 mg/l of edaravone, even more preferably 900-2,000 mg/l of edaravone and most preferably 1,000-1,500 mg/l of edaravone.

The enterally administrable liquid is preferably administered to the human patient in an amount sufficient to provide a dose of 30-300 mg edaravone, more preferably a dose of 60-240 mg edaravone and most preferably a dose of 90-180 mg edaravone.

The enterally administrable liquid that is employed in the present treatment, preferably contains edaravone in aqueous solution. Even more preferably, the enterally administrable liquid is a monophasic solution. Here the term "monophasic" refers to a liquid composition that does not contain two or more distinctive phases. Consequently, the monophasic enterally administrable liquid is not an emulsion (e.g. a micro-emulsion, a nano-emulsion or a micellar suspension/solution).

According to another preferred embodiment, the edaravone present in the enterally administrable liquid is not contained in a clathrate (e.g. a complex with cyclodextrin).

According to another preferred embodiment, the enterally administrable liquid contains less than 3 wt. %, preferably less than 1 wt. % of water-soluble organic solvent selected from polyethylene glycol (e.g. PEG200-10,000), propylene glycol, diethylene glycol monoethyl ether (e.g Transcutol HP, Transcuto lP), polyoxyl castor oils (e.g. Cremophor RH 40, Cremophor EL), polyoxylglycerides (e.g. Labrasol), polyoxyethylene sorbitan fatty acid esters (e.g. Tween 20, Tween 80), water-soluble forms of vitamin E (e.g. TPGS 1000) and ethanol.

The enterally administrable liquid preferably contains not more than 3 wt. %, even more preferably not more than 1 wt. % organic substances other than edaravone and organic water soluble alkalizing agent.

The enterally administrable liquid is typically enterally administered in an amount sufficient to provide a daily dose of 0.4-8 mg edaravone per kg of bodyweight. More preferably, the liquid is enterally administered to provide a daily dose of 0.6-4 mg edaravone per kg of bodyweight, most preferably a daily dose of 1-3 mg edaravone per kg of bodyweight.

In another preferred embodiment of the present treatment the patient has fasted for at least 1 hour before the oral administration of the enterally administrable liquid.

The treatment according to the present invention preferably comprises enterally administering the enterally administrable liquid to the patient at least once daily during a period of at least 2 weeks, more preferably during a period of at least 4 weeks.

The invention is further illustrated by the following non-limiting examples.

EXAMPLES

Example 1

Water dispersible granulates were prepared on the basis of the recipes shown in Table 1.

TABLE 1

|  | wt. % | | |
| --- | --- | --- | --- |
|  | 1.1 | 1.2 | 1.3 |
| Edaravone (micronized) | 9.33 | 9.33 | 9.33 |
| Polaxamer 188 | 2.00 | 5.00 | 8.00 |
| Tris(hydroxymethyl)aminomethane (TRIS) | 8.33 | 8.33 | 8.33 |
| TRIS HCl | 8.33 | 8.33 | 8.33 |
| Mannitol[1] | 72.00 | 69.00 | 66.00 |

[1]Pearlitol ® 200, supplied by Roquette

The micronized edaravone employed had the following particle size distribution (volume distribution measured by laser diffraction):

Dv(10): 1.60 μm
Dv(50): 12.6 μm
Dv(90): 72.6 μm

Edaravone and the excipients were weighed, screened though 1,000 μm sieves and added to a Kenwood chopper mixer and dry blended for 60 seconds. To a 40 g batch purified water was slowly added via a needle and syringe (dropwise) to the blend under mixing. The formulations containing 2%, 5% and 8% of Poloxamer required 6 mL, 5 mL and 4 mL water to obtain suitable wet granules, respectively.

The obtained wet granules were placed in a tray and oven dried at 60° C. for 2 hours. Finally, the granules were passed through a 1,000 μm sieve and the sieved product was stored in amber vials.

The dissolution behaviour of the granulates was evaluated by adding 1.5 g of granulate to 100 ml tap water, thereby providing 140 mg edaravone per 100 ml of water. The granulate was added to a 100 mL volumetric flask containing approx. 80 mL of purified water and mixed on a vortex mixer for 15 seconds three times. The solution was then made up to 100 mL.

It was found that all three granulates dissolved quickly and produced a clear solution.

Example 2

Powder mixtures were prepared on the basis of the recipes shown in Table 2.

TABLE 2

| | mg | | | | |
|---|---|---|---|---|---|
| | 2.1 | 2.2 | 2.3 | 2.4 | 2.5 |
| Edaravone[1] | 140 | 140 | 140 | 140 | 140 |
| Mannitol | | 140 | 560 | | |
| Sorbitol | | | | 140 | 560 |

[1]Non-micronised. Particle size distribution (volume distribution, measured by laser diffraction): Dv(10): 36.7 μm Dv(50): 240 μm Dv(90): 425 μm Edaravone and the excipients were weighed and added to a separate weigh boat where they were lightly blended using a spatula. The blends were added to a 100 mL volumetric flask containing approx. 80 mL of purified water and mixed on a vortex mixer for 15 seconds three times. The solutions were then made up to 100 mL. Observations of the dissolution state was made after completion of the sample and again after 1 and 8 hours.

It was found that all powders produced a suspension that rapidly formed a sediment (Edaravone particles). After 8 hours, upon visual inspection, no changes were seen.

Example 3

Powder mixtures were prepared on the basis of the recipes shown in Table 3 using the procedure described in Example 2.

TABLE 3

| | mg | |
|---|---|---|
| | 3.1 | 3.2 |
| Edaravone[1] | 140 | 140 |
| Mannitol | 546 | 525 |
| Sodium lauryl sulphate | 14 | |
| Poloxamer 188 | | 35 |

[1]Non-micronised. Particle size distribution (volume distribution, measured by laser diffraction): Dv(10): 36.7 μm Dv(50): 240 μm Dv(90): 425 μm The dissolution behaviour of the blends was investigated in the same way as described in Example 2.

It was found that both powders produced a suspension that rapidly formed a sediment (Edaravone particles). After 8 hours upon visual inspection, no changes were seen.

Example 4

Edaravone was wet granulated using an aqueous suspension of sodium lauryl sulphate as granulation liquid. Edaravone was weighed and added to a mortar. SLS was then weighed and dissolved in purified water forming a white suspension. The mass of SLS used was calculated to yield a granulate containing 35 parts by weight edaravone and 6 parts by weight SLS.

The SLS suspension was added to the edaravone via an atomized syringe while mixing in the pestle and mortar forming a slurry. The slurry was then passed through a 500 μm sieve and dried at 60° C. for 2 hours.

The dried granules were then milled down using the pestle and mortar and the finer sized powder was passed through a 75 μm sieve. The resulting fine powder (edaravone/SLS) was stored in a snap cap vile in dark ambient conditions.

Powder mixtures were prepared on the basis of the recipes shown in Table 4 using the procedure described in Example 2.

TABLE 4

| | mg | | |
|---|---|---|---|
| | 4.1 | 4.2 | 4.3 |
| Edaravone/SLS | 164 | 164 | 164 |
| Mannitol | 1036 | 536 | 736 |
| Sodium orthophosphate | — | 500 | 300 |

The dissolution behaviour of these blends was investigated in the same way as described in Example 2.

Blend 4.1 produced a cloudy suspension having a pH of 4.7 that remained cloudy after 8 hours.

Blends 4.2 and 4.3 produced clear solutions. Blend 4.2 was found to dissolve slightly more rapidly than blend 4.3. The solution prepared with blend 4.2 had pH 7.5.

Example 5

Water dispersible granulates were prepared on the basis of the recipes shown in Tables 5a and 5b.

TABLE 5a

| | wt. % |
|---|---|
| Edaravone (micronized) | 8.0 |
| Mannitol | 58.2 |
| Sodium orthophosphate | 33.3 |
| Sodium lauryl sulphate | 0.5 |
| Total | 100.0 |

TABLE 5b

| | wt. % |
|---|---|
| Edaravone (micronized) | 6.0 |
| Mannitol | 80.9 |
| Poloxamer 407 | 0.6 |
| Tris(hydroxymethyl) amino methane | 6.25 |
| Tris(hydroxymethyl) amino methane HCl | 6.25 |
| Total | 100.0 |

A study was conducted in which these granlulates 5a and 5b were dissolved in water and orally administered to dogs. Bioavailability of the orally administered edaravone was compared to intravenously administered edaravone. In each case 60 mg edaravone was administered in a single dose.

The study was conducted in a group of 4 male beagle dogs. Animals were given a single oral administration of an aqueous solution of each of the aforementioned edaravone granulates (1000 mg of granulate 5a in 50 mL or 750 mg of granulate 5b dissolved in 50 mL) or a single intravenous administration of edaravone as two Radicut® ampoules (each ampoule containing 30 mg edaravone/20 ml solution).

Blood samples were taken just before and at regular intervals after administration, and the edaravone plasma concentration of each sample was determined. The averaged results of these measurements are shown in Table 6. Mean parameters indicative of the relative bioavailability are presented in Table 7.

TABLE 6

| Time (hrs) | Edaravone plasma concentration (ng/ml) | | |
|---|---|---|---|
| | Oral administration (granulate 5a) | Oral administration (granulate 5b) | i.v. infusion |
| Pre | 0 | 0 | 0 |
| 0.083 | 532 | 479 | 3060 |
| 0.17 | 318 | 319 | n.d. |
| 0.25 | 210 | 304 | 4383 |
| 0.5 | 200 | 184 | 648 |
| 1 | 142 | 99 | 140 |
| 1.5 | 93 | 45 | n.d. |
| 2 | 68 | 34 | 49 |
| 4 | 25 | 17 | 17 |
| 6 | 12 | 9 | n.d. |
| 8 | n.d. | n.d. | 6 |
| 10 | n.d. | n.d. | 5 | nd.: not determined

TABLE 7

| | Oral administration (granualte 5a) | Oral administration (granulate 5b) | i.v. Infusion |
|---|---|---|---|
| $T_{max}$ (min)[1] | 5 | 5 | 15 |
| $C_{max}$ (ng/ml) | 532 | 506 | 4380 |
| $AUC_{last}$ (h · ng/ml)[2] | 430 | 333 | 1600 |
| $AUC_{0-inf}$ (h · ng/ml)[3] | 500 | 308 | 1630 |

[1]Median
[2]$AUC_{last}$ is the area under the plasma concentration-time curve from time of administration until the last measurable plasma concentration
[3]$AUC_{0-inf}$ is the area under the plasma concentration-time curve from time of administration until (extrapolated) infinity These results demonstrate that orally administered edaravone exhibits rapid absorption with peak maximum concentrations reached at about 5 min after administration. Furthermore the results show that the aqueous edaravone solutions prepared with the granulates according to the invention had a surprisingly high systemic oral bioavailability.

The invention claimed is:

1. A method of administering edaravone to a subject in need thereof, comprising:
 (a) dispersing a pharmaceutical composition comprising edaravone (3-methyl-1-phenyl-2-pyrazolin-5-one) into an aqueous liquid to produce a pharmaceutical liquid comprising at least 0.5 grams of the pharmaceutical composition and at least 0.3 g/l of edaravone, followed by
 (b) enterally administering the pharmaceutical liquid to a human patient in an amount providing a dose of 30-300 mg edaravone, the pharmaceutical composition comprising:
  (i) 2-50 wt. % of edaravone; and
  (ii) 3-50 wt. % of water soluble alkalizing agent;
 wherein the edaravone in the pharmaceutical composition fully dissolves in a solution when the composition is added to demineralized water of 25° C. in a concentration equivalent to an edaravone concentration of 1.4 g/l, and wherein the pH of the solution at 25° C. is at least 0.5 pH units higher than the pH of a solution having the same edaravone concentration and consisting exclusively of edaravone and demineralized water.

2. The method according to claim 1, wherein the pharmaceutical composition is a powder or a tablet.

3. The method according to claim 1, wherein the composition further comprises 25-95 wt. % of one or more excipients selected from the group consisting of filler, disintegrant, effervescent, and binder.

4. The method according to claim 3, wherein the composition further comprises at least 30 wt. % of one or more polyols selected from the group consisting of mannitol, sorbitol, xylitol, maltitol, and lactitol.

5. The method according to claim 1, wherein the composition further comprises 0.5-15 wt. % of surfactant.

6. The method according to claim 5, wherein the composition comprises at least 0.5 wt. % nonionic surfactant.

7. The method according to claim 1, wherein at least 90 vol. % of the edaravone is present in the form of micronized particles having a particle size of less than 100 micrometer.

8. The method according to claim 1, wherein the composition comprises less than 1 wt. % water-insoluble material.

9. The method according to claim 1, wherein the water-soluble alkalizing agent is selected from the group consisting of oxides and hydroxides of alkaline metals; oxides and hydroxides of alkali-earth metals; $Al(OH)_3$; $Fe_2O_3$; salts of weak organic and weak inorganic acids, alkaline amines; alkaline amino acids; and combinations thereof.

10. The method according to claim 1, wherein the water-soluble alkalizing agent has a pKa of at least 7.

11. The method according to claim 1, wherein the edaravone present in the pharmaceutical liquid is not contained in a clathrate.

12. The method according to claim 1, wherein the pharmaceutical liquid comprises less than 3 wt. % of water-soluble organic solvent selected from the group consisting of polyethylene glycol, propylene glycol, diethylene glycol monoethyl ether, polyoxyl castor oils, polyoxylglycerides, polyoxyethylene sorbitan fatty acid esters, water-soluble forms of vitamin E and ethanol.

13. The method according to claim 1, wherein the pharmaceutical liquid is a monophasic solution.

14. The method according to claim 1, wherein 1 part by weight of the pharmaceutical composition is dispersed into 20 to 200 parts by weight of the aqueous liquid.

15. The method according to claim 1, wherein the pharmaceutical liquid comprises at least 500 mg/l of edaravone.

16. The method according to claim 15, wherein the pharmaceutical liquid comprises 800-3,000 mg/l of edaravone.

17. The method according to claim 1, wherein the subject in need suffers from a disease selected from the group consisting of neurodegenerative diseases, auto-immune diseases, myocardial infarction and cerebrovascular diseases.

18. The method according to claim 17, wherein the subject in need thereof suffers from a neurodegenerative disease or cerebrovascular disease.

19. The method according to claim 18, wherein the subject in need thereof suffers from a disease selected from the group consisting of cerebral amyloid angiopathy (CAA), amyotrophic lateral sclerosis (ALS), and Alzheimer's disease.

20. The method according to claim 19, wherein the subject in need thereof suffers from amyotrophic lateral schlerosis (ALS) or Alzheimer's disease.

\* \* \* \* \*